United States Patent [19]

Miyake et al.

[11] Patent Number: 4,913,895
[45] Date of Patent: Apr. 3, 1990

[54] ORAL COMPOSITION

[75] Inventors: Mikio Miyake; Akinori Takahashi, both of Kanagawa, Japan

[73] Assignee: Lion Corporation, Tokyo, Japan

[21] Appl. No.: 76,211

[22] Filed: Jul. 22, 1987

[30] Foreign Application Priority Data

Jul. 24, 1986 [JP] Japan ................. 61-174026

[51] Int. Cl.⁴ .......................... A61K 7/16; A61K 7/26
[52] U.S. Cl. ...................... 424/57; 424/49; 424/52; 424/58
[58] Field of Search ................. 424/57, 128

[56] References Cited

U.S. PATENT DOCUMENTS

| | | | |
|---|---|---|---|
| 4,048,300 | 9/1977 | Tomlinson et al. | 424/57 |
| 4,088,752 | 5/1978 | Muhlemann et al. | 424/57 |
| 4,132,773 | 1/1979 | Best et al. | 424/57 |
| 4,203,966 | 5/1980 | Faunce | 424/57 |
| 4,224,307 | 9/1980 | Thiele et al. | 424/57 |
| 4,279,888 | 7/1981 | Suganuma et al. | 424/57 |
| 4,460,565 | 7/1984 | Weststrabe et al. | 424/57 |
| 4,515,770 | 5/1985 | Besic | 424/57 |

FOREIGN PATENT DOCUMENTS

| | | |
|---|---|---|
| 0002184 | 10/1978 | European Pat. Off. |
| 0097476 | 1/1984 | European Pat. Off. |
| 0236290 | 9/1987 | European Pat. Off. |
| 0249398 | 12/1987 | European Pat. Off. |
| 0254452 | 1/1988 | European Pat. Off. |
| 0295116 | 12/1988 | European Pat. Off. |
| 0297211 | 1/1989 | European Pat. Off. |
| 0309414 | 3/1989 | European Pat. Off. |
| 2445676 | 9/1974 | Fed. Rep. of Germany |
| 2752852 | 5/1979 | Fed. Rep. of Germany ........ 424/57 |
| 3526654 | 7/1985 | Fed. Rep. of Germany |
| 2130275 | 3/1972 | France |
| 2297631 | 1/1976 | France |
| 52-108029 | 9/1977 | Japan |
| 53-133642 | 11/1978 | Japan |
| 58-018315 | 2/1983 | Japan ........................... 424/57 |
| 59-1409 | 1/1984 | Japan |
| 59-42311 | 3/1984 | Japan |
| 2102289 | 6/1982 | United Kingdom |
| 2182244 | 5/1987 | United Kingdom |
| 2188548 | 10/1987 | United Kingdom |
| 2201593 | 9/1988 | United Kingdom |
| 2204487 | 11/1988 | United Kingdom |

*Primary Examiner*—Shep K. Rose
*Attorney, Agent, or Firm*—Birch, Stewart, Kolasch & Birch

[57] ABSTRACT

An oral composition comprising (i) at least one phosphate selected from the group consisting of linear polyphosphates of the formula (I):

$$M_{n+2}P_nO_{3n+1} \qquad (I)$$

wherein M represents Na or K and N $\geq 2$, and cyclic polyphosphates of the formula (II):

$$(M'PO_3)_m \qquad (II)$$

wherein M' represents Na or K and m $\geq 3$ and (iii) l-menthol, anethol, or the mixture thereof in an aqueous medium. This oral composition has an excellent antibacterial effect and prevents the development of calculus and periodontal diseases.

19 Claims, No Drawings

ORAL COMPOSITION

BACKGROUND OF THE INVENTION

1. Field of the Invention

The present invention relates to an oral composition having an excellent antibacterial action agent *Actinomyces viscosus* and effectively preventing the development of calculus and periodontitis.

2. Description of the Related Art

Calculus is a hard deposit, having a high inorganic content, formed on the surfaces of teeth, and is believed to be a major cause of the development of gingivitis and periodontis. Accordingly, an inhibition of the formation of calculus effectively prevents and cures the development of periodontal diseases. The rapid deposition of calculus can be prevented to a certain extent by brushing the teeth at frequent intervals. However, brushing alone is not sufficient for removing substantially all of the calculus deposited on the teeth.

The formation of calculus is considered to be caused by the deposition of amorphous or microcrystalline calcium phosphate on membraneous portions of bacteria or the substances between bacteria in the plaque, which gradually become dense and change to hydroxyapatite. It is known that the main bacteria forming organic matrixes in old plaque or plaques in gingival sulcus, in which the above-mentioned calcification occurs are filamentous bacteria or rod-shaped bacteria belonging to Actinomyces, Leptotrichia, Bacteroides, and Fusobacterium. Accordingly, an inhibition of a growth of these bacteria will effectively suppress the formation of calculus, and thus prevent the development of periodontal diseases.

The inhibition of the formation of plaque, and the removal of the plaque, are most important for calculus prevention, and to this end, physical methods such as brushing have been used. As mentioned above, brushing alone is not sufficient to prevent and remove calculus and, therefore, chemical methods using antibacterials such as chlorohexidine, benzalkonium chloride, and cetylpyridinium chloride have been used. However, these antibacterials can not be formulated at a higher amount, from the viewpoint of safety.

Furthermore, it is known that polyphosphates have inhibited the caries in animal tests (e.g., Journal of Dental Research, Vol. 43, p 1123-1136) and also possess antibacterial activity against *Streptococcus mutans* and Diphtheroids (e.g., Arch. Oral Biol. Vol. 27, p 809-816, 1982 and Infection and Immunity, Vol. 1, p 604-606, 1970). Furthermore, Arch. Oral Biol., Vol. 15, p 893-896 (1970) discloses the effectiveness of a water-soluble phosphate against the formation of calculus. In addition to the above, JP-A-52-108029 (Kokai) proposes the prevention of the formation of calculus by a combination of polyphosphates and polyvalent cations, and JP-A-59-42311 proposes an oral composition formulated with pyrophosphate of anticalculus. Thus, it is known in the art that the use of polyphosphates in oral compositions is effective for the inhibition.

However, the effects obtained from the use of polyphosphates per se are not sufficient and, therefore, there is a strong demand for the development of oral compositions having an excellent calculus preventive effect or an effective antibacterial action against filamentous bacteria.

SUMMARY OF THE INVENTION

Accordingly, the objects of the present invention are to eliminate the above-mentioned disadvantages of the prior art and to provide an oral composition having an excellent antibacterial effect and capable of effectively preventing the development of calculus and periodontal diseases.

Other objects and advantages of the present invention will be apparent from the following description.

In accordance with the present invention, there is provided an oral composition comprising (i) at least one phosphate selected from the group consisting of linear polyphosphates of the formula (I):

$$M_{n+2}P_nO_{3n+1} \qquad (I)$$

wherein M represents Na or K and $n \geq 2$, and cyclic polyphosphates of the formula (II):

$$(M'PO_3)_m \qquad (II)$$

wherein M' represents Na or K and $m \geq 3$ and (ii) l-menthol, anethol, or the mixture thereof in an aqueous medium.

DESCRIPTION OF THE PREFERRED EMBODIMENTS

The present inventors have studied ways in which to accomplish the above-mentioned objects, and as a result, found that, when l-menthol and/or anethol are used in combination with the polyphosphates, especially those having the above-mentioned formula (I) or (II), these components synergistically function to provide a remarkable antibacterial effect against *Actinomyces viscosus* which forms plaques susceptible to calcification. Thus, the growth of *Actinomyces viscosus* is inhibited and the development of calculus and periodontal diseases is effectively prevented.

The oral composition according to the present invention includes, as a component (i) for inhibiting the growth of *Actinomyces viscosus* and for suppressing the formation of calculus, a polyphosphate having the above-mentioned formulae (I) and (II). Examples of the linear polyphosphates having the formula (I) are those having an n of 2 in the formula (I), such as sodium pyrophosphate and potassium pyrophosphate, those having an n of 3 in the formula (I), such as sodium tripolyphosphate and potassium tripolyphosphate, those having an n of 4 in the formula (I), such as sodium tetrapolyphosphate and potassium tetrapolyphosphate, and those having a high polymerization degree such as sodium metaphosphate and potassium metaphosphate. Examples of the cyclic polyphosphates having the formula (II) are those having an m of 3 in the formula (II), such as sodium trimetaphosphate and potassium trimetaphosphate, those having an m of 4 in the formula (II), such as sodium tetrametaphosphate and potassium tetrametaphosphate, and those having an m of 6 in the formula (II), such as sodium hexametaphosphate and potassium hexametaphosphate. These polyphosphates may be used alone or in any mixture thereof. Of these polyphosphates, linear polyphosphates, preferably those having an n of 3 or more in the formula (I), are especially used because of their better antibacterial properties.

Although there are no specific limitations to the amount of the polyphosphate to be formulated into the present oral composition, preferably the polyphosphate is formulated in an amount of 0.1% to 10% by weight, preferably 0.5% to 5% by weight, based on the total amount of the present oral composition. When the amount of the polyphosphate is less than 0.1% by weight, the desired synergic effect thereof with l-menthol and/or anethol is decreased. Conversely, when the amount of the polyphosphate is more than 10% by weight, the taste of the present oral composition becomes unpleasant.

As mentioned above, according to the present invention, l-menthol and/or anethol are used in combination with the above-mentioned polyphosphates. The l-menthol and/or anethol usable in the present invention may include those isolated from essential oil or synthesized l-menthol and/or anethol. Furthermore, essential oils containing l-menthol such as Japanese mint oil, peppermint oil, and Mitcham peppermint oil, or those containing anethol such as Anise oil, Fennel oil, and Star anise oil, may be directly used, without isolating l-menthol or anethol therefrom. The l-menthol and anethol may be used alone or in any mixture thereof. Furthermore, the isolated or synthesized l-menthol and/or anethol may be used in combination with the above-mentioned essential oil, per se.

Although there are no critical limitations to the amount of l-menthol and/or anethol to be formulated into a present oral composition, preferably the l-menthol and/or anethol is formulated in an amount of 0.01% to 2% by weight, preferably 0.05% to 1% by weight, based on the total weight of the oral composition. When the amount of l-menthol and/or anethol is less than 0.01% by weight, the synergic effect thereof with the polyphosphate is not felt, and the growth of $actinomyces\ viscosus$ is not inhibited. Conversely, when the amount of l-menthol and/or anethol to be formulated into the present oral composition is more than 2% by weight, the practical value as an oral composition is diminished.

The oral composition according to the present invention may contain, in addition to the l-menthol and/or anethol, other essential oils such as spearmint oil (e.g., native type, scotch type) and various flavoring materials such as carvone and eugenol.

The oral compositions according to the present invention may optionally contain, in addition to the above-mentioned essential constituents, any conventional ingredients depending upon, for example, the kinds of the oral compositions and the use thereof.

For example, abrasives such as calcium phosphate (dibasic), calcium carbonate, calcium pyrophosphate, insoluble sodium metaphosphate, aluminum oxide, aluminum hydroxide, silica, silicates and resins; binders such as sodium carboxymethyl cellulose, hydroxyethyl cellulose, alginate, carageenan, gum arabic, polyvinyl alcohol, and colloidal silica; humectants such as polyethylene glycol, sorbitol, glycerol, and propylene glycol; surfactants such as sodium lauryl sulfate, sodium dodecylbenzene sulfonate, sodium hydrogenated cococut fatty acid monoglyceride monosulfate, sodium laurylsulfo acetatate, sodium lauroyl sarcosinate, N-acyl glutamate, lauryl diethanolamide, and sucrose fatty acid ester; sweeteners such as saccharin sodium stebiocide, neohesperidyl dihydrochalcon, glycyrrhizin, perillartine, and p-methoxy cinnamic aldehyde; preservatives; coloring agents; effective components such as chlorohexidines, dextranase, mutanase, sorbin acid, alexidine, hinokitiol, cetyl pyridinium chloride, alkylglycines, alkyldiaminoethyl glycine salts, allantoin, ε-aminocaproic acid, tranexamic acid, azulene, vitamin E, water-soluble monobasic or dibasic phosphates, quaternary ammonium compounds and sodium chloride may be formulated into the present oral composition. Still other components such as sodium fluoride, sodium monofluorophosphate, and stannous fluoride may be formulated into the present oral compositions.

The oral compositions according to the present invention may be prepared in any conventional manner by, for example, mixing the above-mentioned essential and optional ingredients with water.

According to the present invention, the oral composition having synergic antibacterial effects against $Actinomyces\ viscosus$ and having excellent preventive effects on the development of calculus and periodontal diseases can be provided by formulating the specified polyphosphate and l-menthol and/or anethol into the oral composition.

EXAMPLES

The present invention will now be further illustrated by, but is by no means limited to, the following Experiments and Examples, wherein "%" means "% by weight" unless otherwise specified.

EXPERIMENT 1

Culture media containing, as a polyphosphate, 0.04% of sodium pyrophosphate ($Na_4P_2O_7$), sodium tripolyphosphate ($Na_5P_3O_{10}$), sodium trimetaphosphate [$(NaPO_3)_3$], and sodium metaphosphate ($Na_{n+2}P_nO_{3n+1}$; n=12 and 58), a culture medium containing 0.025% of l-menthol, and culture media containing 0.04% of the above-mentioned polyphospholates and 0.025% of l-menthol were prepared. Subculture $Actinomyces\ viscosus$ 19246 was inoculated into these media and incubated at a temperature of 37° C. for 2 days under an aneorbic condition (i.e., 80% $N_2$, 10% $H_2$, 10% $CO_2$). The volume of the inoculated bacterial solution was one hundred of the media. The degree of bacterial growth was monitored by measuring the optical density at 550 nm. A Todd Hewitt broth (DIFCO Laboratories) was used as the basal medium.

The results are shown in Table 1.

TABLE 1

| Polyphosphate | Addition of l-Menthol | |
|---|---|---|
| | No | Yes |
| None | 0.85 | 0.72 |
| Sodium pyrophosphate | 0.75 | 0.40 |
| Sodium tripolyphosphate | 0.60 | 0.15 |
| Sodium trimetaphosphate | 0.78 | 0.50 |
| Sodium metaphosphate (n = 12) | 0.58 | 0.05 |
| Sodium metaphosphate (n = 58) | 0.50 | 0.05 |

EXPERIMENT 2

Culture media containing, as a polyphosphate, 0.04% potassium pyrophosphate ($K_4P_2O_7$), sodium tripolyphosphate ($Na_5P_3O_{10}$), sodium tetrapolyphosphate ($Na_6P_4O_{13}$), and sodium metaphosphate ($Na_{n+2}P_nO_{3n+1}$, n=40 and 128), and a culture medium containing 0.03% of anethol, culture media containing the above-mentioned polyphosphates and 0.03% of anethol were prepared. Subcultured $Actinomyces\ visdcosus$ 19246 was inoculated into these media and incubated at a temperature of 37° C. for 2 days under an anaerobic condition (i.e., 80% $N_2$, 10% $H_2$, 10% $CO_2$). The volume of the inoculated bacterial solution was one hundred of the media. The degree of the bacterial growth was monitored by measuring the optical density at 550 nm. The culture broth used was the same as that used in Experiment 1.

The results are shown in Table 2.

TABLE 2

| Polyphosphate | Addition of Anethol | |
|---|---|---|
| | No | Yes |
| None | 0.85 | 0.74 |
| Potassium pyrophosphate | 0.75 | 0.38 |
| Sodium tripolyphosphate | 0.60 | 0.12 |
| Sodium trimetaphosphate | 0.78 | 0.46 |
| Sodium tetrapolyphosphate | 0.63 | 0.06 |
| Sodium metaphosphate (n = 40) | 0.52 | 0.08 |
| Sodium metaphosphate (n = 128) | 0.56 | 0.11 |

As is clear from the results shown in Tables 1 and 2, the growth of *Actinomyces viscosus* is inhibited by the synergic action of the polyphosphates in combination with l-menthol or anethol. Thus, it is revealed that the use of the polyphosphate in combination with l-menthol or anethol provides an excellent antibacterial action against the *Actionomyces viscosus*. Furthermore, when sodium tripolyphosphate or linear polyphosphates having a polymerization degree greater than that of tripolyphosphate are used in combination with l-menthol or anethol, more improved synergic effects are provided and thus a particularly effective antibacterial action can be obtained.

Example 1: Mouth wash

| Ingredient | % |
|---|---|
| Ethanol | 20.0 |
| Saccharin sodium | 0.05 |
| l-Menthol | 1.5 |
| Anethol | 0.1 |
| Tetrasodium pyrophosphate | 3.0 |
| Chlorohexidine hydrochloride | 0.025 |
| Lauryl diethanolamide | 0.3 |
| Water | balance |
| | 100.0% |

Example 2: Mouth wash

| Ingredient | % |
|---|---|
| Ethanol | 10.0 |
| 85% Glycerol | 10.0 |
| Saccharin sodium | 0.05 |
| Polyoxyethylene hydrogenated castor oil derivative | 1.0 |
| l-Menthol | 0.5 |
| Sodium metaphosphate (n = 56) | 5.0 |
| Sodium fluoride | 0.22 |
| Water | balance |
| | 100.0% |

Example 3: Aqueous dentifrice

| Ingredient | % |
|---|---|
| Glycerol | 35.0 |
| Carageenan | 1.5 |
| Peppermint oil | 0.7 |
| Sodium trimetaphosphate | 1.0 |
| Sodium monofluorophosphate | 0.76 |
| Ethanol | 1.0 |
| Water | balance |
| | 100.0% |

Example 4: Toothpaste

| Ingredient | % |
|---|---|
| Calcium phosphate (dibasic).dihydride | 50.0 |
| 85% Glycerol | 20.0 |
| Propylene glycol | 4.0 |
| Sodium carboxymethyl cellulose | 1.2 |
| Potassium pyrophosphate | 2.0 |
| Sodium monofluorophosphate | 0.76 |
| Sodium lauryl sulfate | 1.5 |
| Saccharin sodium | 0.1 |
| l-Menthol | 1.0 |
| Water | balance |
| | 100.0% |

Example 5: Toothpaste

| Ingredient | % |
|---|---|
| Silicic anhydride | 25.0 |
| 60% Sorbitol | 20.0 |
| Thickening silica | 2.0 |
| Propylene glycol | 4.0 |
| Sodium carboxymethyl cellulose | 1.5 |
| Sodium tripolyphosphate | 1.5 |
| Anethol | 0.2 |
| Peppermint oil | 1.0 |
| Sodium fluoride | 0.21 |
| Sodium lauryl sulfate | 1.2 |
| Saccharin sodium | 0.1 |
| Water | balance |
| | 100.0% |

Example 6: Toothpaste

| Ingredient | % |
|---|---|
| Aluminum hydroxide | 30.0 |
| 85% Glycerol | 20.0 |
| Polyethylene glycol 400 | 5.0 |
| Sodium carboxymethyl cellulose | 1.2 |
| Sodium metaphosphate (n = 36) | 5.0 |
| Spearmint oil | 1.0 |
| Anethol | 0.1 |
| Dextranase | 0.18 |
| α-Olefin sulfonate | 1.0 |
| Saccharin sodium | 0.1 |
| Water | balance |
| | 100.0% |

Example 7: Toothpaste

| Ingredient | % |
|---|---|
| Silicic acid | 20.0 |
| Titanium dioxide | 2.0 |
| 60% Sorbitol | 25.0 |
| Propylene glycol | 4.0 |
| Sodium carboxymethyl cellulose | 1.2 |
| Sodium metaphosphate (n = 59) | 4.0 |
| Japanese mint oil | 0.7 |
| Anethol | 0.3 |
| Eugenol | 0.1 |
| Chlorhexidine gluconate | 0.025 |
| Sodium lauryl sulfate | 1.2 |
| Saccharin sodium | 0.1 |
| Water | balance |
| | 100.0% |

Example 8: Toothpaste

| Ingredient | % |
|---|---|
| Silicic anhydride | 30.0 |
| 60% Sorbitol | 25.0 |
| Thickening silica | 2.0 |
| Propylene glycol | 4.0 |
| Sodium carboxymethyl cellulose | 1.5 |
| Sodium metaphosphate (n = 128) | 2.0 |
| l-Menthol | 0.1 |
| Spearmint oil | 0.8 |
| Tranexamic acid | 0.05 |
| Glycyrrhizin | 0.01 |
| Saccharin sodium | 0.1 |
| Sodium lauryl sulfate | 1.2 |
| Water | balance |
| | 100.0% |

Example 9: Toothpaste

| Ingredient | % |
|---|---|
| Calcium phosphate (dibasic).dihydrate | 40.0 |
| 85% Glycerol | 25.0 |
| Thickening silica | 2.0 |
| Propylene glycol | 4.0 |

| -continued | |
| --- | --- |
| Sodium carboxymethyl cellulose | 1.2 |
| Sodium polyphosphate (n = 3.2) | 1.0 |
| Potassium polyphosphate (n = 3.1) | 2.0 |
| l-Menthol | 0.5 |
| Anethol | 0.3 |
| ξ-Aminocaproic acid | 0.01 |
| Dihydroxy aluminum allantoin | 0.01 |
| Saccharin sodium | 0.1 |
| Sodium lauryl sulfate | 1.2 |
| Water | balance |
| | 100.0% |

| Example 10: Toothpaste | |
| --- | --- |
| Ingredient | % |
| Silicic anhydride | 25.0 |
| 60% Sorbitol | 25.0 |
| Thickening silica | 2.0 |
| Polyethylene glycol 400 | 4.0 |
| Sodium carboxymethyl cellulose | 1.2 |
| Sodium tetrapolyphosphate | 3.0 |
| Peppermint oil | 0.8 |
| Anise oil | 0.1 |
| Sodium fluoride | 0.21 |
| Chlorhexidine hydrochloride | 0.01 |
| Sodium lauryl sulfate | 1.2 |
| Saccharin sodium | 0.1 |
| Water | balance |
| | 100.0% |

| Example 11: Toothpaste | |
| --- | --- |
| Ingredient | % |
| Silicic anhydride | 23.0 |
| 85% Glycerol | 20.0 |
| Thickening silica | 2.0 |
| Polyethylene glycol 400 | 4.0 |
| Sodium carboxymethyl cellulose | 1.2 |
| Sodium metaphosphate (n = 14) | 3.0 |
| l-Menthol | 0.5 |
| Peppermint oil | 0.5 |
| Anethol | 0.2 |
| Sodium monofluorophosphate | 0.76 |
| Sodium lauryl sulfate | 1.2 |
| Saccharin sodium | 0.1 |
| Water | balance |
| | 100.0% |

| Example 12: Toothpaste | |
| --- | --- |
| Ingredient | % |
| Silicic anhydride | 25.0 |
| 85% Glycerol | 23.0 |
| Thickening silica | 2.0 |
| Propylene glycol | 4.0 |
| Sodium carboxymethyl cellulose | 1.2 |
| Sodium metaphosphate | 2.0 |
| Potassium metaphosphate | 2.0 |
| Spearmint oil | 0.5 |
| Peppermint oil | 0.5 |
| Sodium fluoride | 0.21 |
| Sodium lauryl sulfate | 1.2 |
| Saccharin sodium | 0.1 |
| Water | balance |
| | 100.0% |

We claim:

1. In the art of inhibiting *Actinomyces viscosus* and the formation of hard deposits of calculus on the surfaces of teeth, and to thereby prevent the development of gingivitis and periodontal disease, by contacting the teeth and *Actinomyces viscosus* with oral hygiene toothpaste or mouthwash compositions formulated to contain 0.1 to 10% by weight, based on the total amount of the oral hygiene composition, of component (i) which is a polyphosphate selected from the group consisting of sodium pyrophosphate, potassium pyrophosphate, sodium tripolyphosphate, potassium tripolyphosphate, sodium tetrapolyphosphate, potassium tetrapolyphosphate, sodium metaphosphate, potassium metaphosphate, sodium trimetaphosphate, potassium trimetaphosphate, sodium tetrametaphosphate, potassium tetrametaphosphate, sodium hexametaphosphate, and mixtures potassium hexametaphosphate, the synergistically effective improvement consisting of the step of including with said anti-calculus polyphosphate 0.01% to 2% by weight, based on the total amount of the oral hygiene composition, of component (ii) which is a member selected from the group consisting of (a) l-menthol, (b) anethol and (c) mixtures of (a) and (b), in order to exert a synergistic antibacterial effect against *Actinomyces viscosus*, a plaque-forming bacteria causing the formation of calculus and periodental disease.

2. The method as claimed in claim 1, wherein said component (i) is a linear polyphosphate selected from the group consisting of sodium tripolyphosphate, potassium tripolyphosphate, sodium tetrapolyphosphate, potassium tetrapolyphosphate, sodium metaphosphate, and potassium metaphosphate.

3. The method as claimed in claim 2, wherein component (ii) comprises l-menthol.

4. The method as claimed in claim 2, wherein component (ii) comprises a mixture of l-menthol and anethol.

5. The method as claimed in claim 1, wherein component (ii) comprises l-menthol.

6. The method as claimed in claim 1, wherein component (ii) comprises l-menthol.

7. The method as claimed in claim 1, wherein component (ii) comprises anethol.

8. The method as claimed in claim 1, wherein component (ii) comprises anethol.

9. The method as claimed in claim 1, wherein component (ii) comprises a mixture of l-menthol and anethol.

10. The method as claimed in claim 1, wherein component (ii) comprises a mixture of l-menthol and anethol.

11. The method as claimed in claim 1, wherein the amount of component (i) is 0.5% to 5% by weight based on the total amount of the composition.

12. The method as claimed in claim 2, wherein the amount of said component (i) is 0.5% to 5% by weight based on the total amount of the composition.

13. The method as claimed in claim 1, wherein the amount of component (ii) is 0.05% to 1% by weight based on the total amount of the composition.

14. The method as claimed in claim 11, wherein the amount of component (ii) is 0.05% to 1% by weight based on the total amount of the composition.

15. The method as claimed in claim 12, wherein the amount of component (ii) is 0.05% to 1% by weight based on the total amount of the composition.

16. The method as claimed in claim 1, wherein component (ii) comprises l-menthol.

17. The method as claimed in claim 1, wherein component (ii) comprises anethol.

18. The method as claimed in claim 1, wherein component (ii) comprises a mixture of l-menthol and anethol.

19. The method as claimed in claim 2, wherein component (ii) comprises anethol.

* * * * *